US011096958B2

(12) United States Patent
Burke et al.

(10) Patent No.: US 11,096,958 B2
(45) Date of Patent: Aug. 24, 2021

(54) SODIUM CHLORITE COMPOSITIONS WITH ENHANCED ANTI-MICROBIAL EFFICACY AND REDUCED TOXICITY

(71) Applicant: Allergan, Inc., Irvine, CA (US)

(72) Inventors: James A. Burke, Santa Ana, CA (US); Richard S. Graham, Irvine, CA (US); Corine Ghosn, Lake Forest, CA (US); Alexandra Almazan, Santa Ana, CA (US); Michael Engles, San Clemente, CA (US); Lakshmi Rajagopalan, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 16/394,981

(22) Filed: Apr. 25, 2019

(65) Prior Publication Data

US 2019/0328773 A1    Oct. 31, 2019

Related U.S. Application Data

(60) Provisional application No. 62/663,886, filed on Apr. 27, 2018.

(51) Int. Cl.
| *A61K 33/00* | (2006.01) |
| *A61P 31/02* | (2006.01) |
| *A61K 9/00*  | (2006.01) |
| *A61K 47/26* | (2006.01) |

(52) U.S. Cl.
CPC .......... *A61K 33/00* (2013.01); *A61K 9/0014* (2013.01); *A61K 9/0048* (2013.01); *A61K 47/26* (2013.01); *A61P 31/02* (2018.01)

(58) Field of Classification Search
None
See application file for complete search history.

(56) References Cited

U.S. PATENT DOCUMENTS

| 4,084,747 A   | 4/1978  | Alliger |
| 4,330,531 A   | 5/1982  | Alliger |
| 4,499,077 A   | 2/1985  | Stockel |
| 4,689,215 A   | 8/1987  | Ratcliff |
| 4,902,498 A   | 2/1990  | Agricola |
| 5,424,078 A   | 6/1995  | Dziabo |
| 5,489,435 A   | 2/1996  | Ratcliff |
| 5,663,170 A * | 9/1997  | Ushio .............. A61K 47/40 514/231.2 |
| 5,667,817 A   | 9/1997  | Kross |
| 5,782,992 A   | 7/1998  | Frangione |
| 6,017,554 A   | 1/2000  | Ratcliff |
| 6,277,363 B1  | 8/2001  | Ratcliff |
| 6,287,551 B1  | 9/2001  | Ratcliff |
| 6,488,965 B1  | 12/2002 | Karageozian |
| 7,923,469 B2* | 4/2011  | Huth ................ C11D 1/52 514/458 |
| 8,545,898 B2  | 10/2013 | Fukuda |
| 8,784,780 B2  | 7/2014  | Gurge |
| 9,314,528 B2  | 4/2016  | Vehige |
| 9,579,385 B2  | 2/2017  | Gore |
| 9,580,317 B2  | 2/2017  | Mcwhorter |
| 2004/0137079 A1 | 7/2004  | Cook et al. |
| 2004/0185068 A1 | 9/2004  | Yu et al. |
| 2005/0142215 A1 | 6/2005  | Kling |
| 2005/0276867 A1 | 12/2005 | Lyons |
| 2007/0264226 A1 | 11/2007 | Karagoezian |
| 2008/0020064 A1 | 1/2008  | Gilbard |
| 2008/0269353 A1 | 10/2008 | Takada |
| 2011/0212035 A1 | 9/2011  | Gurge |
| 2013/0136805 A1 | 5/2013  | Buyuktimkin |
| 2014/0341871 A1 | 11/2014 | Morris |

FOREIGN PATENT DOCUMENTS

| CN | 106074692 | 11/2016 |
| EP | 1850913   | 9/2009  |
| EP | 2046287   | 11/2011 |
| EP | 1765420   | 6/2017  |
| GB | 1402326   | 8/1975  |
| JP | 4670107   | 1/2011  |
| WO | 0019981   | 4/2000  |

OTHER PUBLICATIONS

Antiseptic Cleansers, Shampoo retrieved from http://veterinarynews.dvm360.com/antiseptic-cleansers-shampoo-0 on Aug. 16, 2017, 2 pages.
Cooper, R., A review of the evidence for the use of topical antimicrobial agents in wound care, Worldwide Wounds, 2004, 1-14.
Ferguson, A., et al., Comparsion of 5% povidone-iodine solution against 1% povidone-iodine solution in preoperative cataract surgery antisepsis: a prospective randomized double blind study, Br. J. Ophthalmol., 2003, 163-167, 87.
Freeman, D, et al., Preservatives in Topical Ophthalmic Medications: Historical and Clinical Perspectives, Expert Rev. Ophthalmol., 2009, 59-64, 4 (1).
Georgiade, G., et al., Efficacy of povidone-iodine in pre-operative skin preparation, J. Hospital Infection, 1985, 67-71, 6 (Suppl).
Heal a Pet Antiseptic Spray (4 oz) retrieved from http://www.healthypets.com/healapetspray.html#tabs-2 on Aug. 16, 2017, 4 pages.
International Search Report & Written Opinion dated Aug. 16, 2019, for PCT/US19/29078 filed on Apr. 25, 2019 in the name of Allergan, Inc.
Lemp, Michael, Report of the National Eye Institute/Industry Workshop on Clinical Trials in Dry Eyes, CLAO, 1995, 221-232, 21.
McDonald, T.O., et al., Eye irritation, Dermatotoxicology, 1987, 641-697, Ch. 32.

(Continued)

*Primary Examiner* — Craig D Ricci
(74) *Attorney, Agent, or Firm* — Michael J. Blessent; Bret E. Field; Bozicevic, Field & Francis LLP

(57) ABSTRACT

Disclosed are antiseptic compositions for disinfecting tissues, in particular for ocular use. Methods and compositions disclosed herein include sodium chlorite, optionally in combination with a surfactant.

12 Claims, 9 Drawing Sheets

(56) References Cited

OTHER PUBLICATIONS

Prusky, G., et al., Rapid Quantification of Adult and Developing Mouse Spatial Vision Using a Virtual Optomotor System, IVOS, 2004, 4611-4616, 45 (12).

Romanowski, E.G., et al., N-Chlorotaurine Is an Effective Antiviral Agent against Adenovirus In Vitro and in the Ad5/NZW Rabbit Ocular Model, IOVS, 2006, 2021-2026, 47 (5).

Trinavarat, A., et al., Reduction of Endophthalmitis Rate after Cataract Surgery with Preoperative 5% Povidone-Iodine, Dermatology, 2006, 35-40, 212 (Suppl).

* cited by examiner

SODIUM CHLORITE COMPOSITIONS WITH ENHANCED ANTI-MICROBIAL EFFICACY AND REDUCED TOXICITY

REFERENCE TO PRIORITY DOCUMENT

This application claims the benefit of priority under 35 U.S.C. § 119(e) of co-pending U.S. provisional patent application Ser. No. 62/663,886, filed Apr. 27, 2018. The disclosure of the provisional patent application is hereby incorporated by reference in its entirety.

BACKGROUND

The most routine type of skin disinfection for surgical procedures is prepping with povidone-iodine, also known as Betadine®. Povidone-iodine is an effective antimicrobial agent against many types of organisms in a variety of settings such as the skin, in wounds, and on the ocular surface. However, povidone-iodine is irritating, particularly when used on the ocular surface. Povidone-iodine causes ocular discomfort and vision loss.

SUMMARY

Implementations disclosed herein include an antiseptic composition for disinfecting tissues, the composition including sodium chlorite. The sodium chlorite can be in an amount of about 800 ppm to about 8000 ppm. The sodium chlorite can be activated in a buffer having a pH that is less than or equal to 5 or up to about 7.6. The composition can further include a surfactant. The surfactant can be a non-ionic surfactant in an amount of between 0.015% w/v to about 0.5% w/v. The non-ionic surfactant can be one or more of polyoxyethylene sorbitan monooleate, polyoxyethylene lauryl ether, or poly(ethylene glycol)-block-poly(propylene glycol)-block-poly(ethylene glycol). The composition can have antimicrobial activity. The composition can be in a form including aqueous solutions, emulsions (oil-in-water or water-in-oil), lotions, creams, ointments, salves, gels, instillations, foams, powders, tinctures, and solids. The composition can be in the form of an eye drop, eye wash, eye swab, or an eye bath. The tissues disinfected can include skin, eye, wound, or incision. The tissues disinfected can include an eye lid, eye brow, cheek, cornea, conjunctiva, or palpebral fornix.

In an interrelated aspect, disclosed are uses of a composition for the preparation of a medicament for the disinfection of tissues. The composition includes sodium chlorite activated in a buffer. The sodium chlorite can be in an amount of about 800 ppm to about 8000 ppm. The buffer can have a pH that is less than or equal to 5 or up to about 7.6. The composition can include a surfactant. The surfactant can be a non-ionic surfactant in an amount of between 0.015% w/v to about 0.5% w/v. The non-ionic surfactant can be one or more of polyoxyethylene sorbitan monooleate, polyoxyethylene lauryl ether, or poly(ethylene glycol)-block-poly(propylene glycol)-block-poly(ethylene glycol). The composition can have antimicrobial activity. The composition can be in a form including aqueous solutions, emulsions (oil-in-water or water-in-oil), lotions, creams, ointments, salves, gels, instillations, foams, powders, tinctures, and solids. The composition can be in the form of an eye drop, eye wash, eye swab, or an eye bath. The tissues disinfected can include skin, skin wound, or skin incision. The tissues disinfected can include an eye lid, eye brow, cheek, cornea, conjunctiva, or palpebral fornix.

In an interrelated aspect, disclosed are methods of treating tissues including topically applying an antiseptic composition comprising sodium chlorite activated in a buffer. The sodium chlorite can be in an amount of about 800 ppm to about 8000 ppm. The sodium chlorite can be activated in a buffer having a pH that is less than or equal to 5. The sodium chlorite can be activated in a buffer having a pH that is up to about 7.6. The antiseptic composition can further include a surfactant. The surfactant can be a non-ionic surfactant in an amount of between 0.015% w/v to about 0.5% w/v. The non-ionic surfactant can include one or more of polyoxyethylene sorbitan monooleate, polyoxyethylene lauryl ether, or poly(ethylene glycol)-block-poly(propylene glycol)-block-poly(ethylene glycol). The antiseptic composition can have antimicrobial activity. The antiseptic composition can be in a form of aqueous solutions, emulsions (oil-in-water or water-in-oil), lotions, creams, ointments, salves, gels, instillations, foams, powders, tinctures, and solids. The antiseptic composition can be in the form of an eye drop, eye wash, eye swab, or an eye bath. The tissues disinfected can include skin, eye, skin wound, or skin incision. The tissues disinfected can include an eye lid, eye brow, cheek, cornea, conjunctiva, or palpebral fornix. The antiseptic compositions described herein can be for uses such as the treatment of tissues.

In an interrelated aspect, disclosed are ophthalmically acceptable topical compositions for disinfecting ocular tissue. The composition includes sodium chlorite in an amount of about 800 ppm to about 8000 ppm; a surfactant in an amount of about 0.015% w/v to about 0.5% w/v; and at least one buffer. The surfactant can be polyoxyethylene sorbitan monooleate. The composition can include about 8000 ppm sodium chlorite, about 0.5% w/v polyoxyethylene sorbitan monooleate, about 0.83% w/v sodium phosphate monobasic monohydrate, about 0.17% w/v citric acid monohydrate, hydrochloric acid and/or sodium hydroxide, and water, and the composition can have a pH of about 5. The composition can include about 8000 ppm sodium chlorite, about 0.5% w/v polyoxyethylene sorbitan monooleate, about 0.25% w/v sodium phosphate monobasic monohydrate, about 0.35% w/v citric acid monohydrate, and water, and the composition can have a pH of about 4. The composition can include about 8000 ppm sodium chlorite, about 0.5% w/v polyoxyethylene lauryl ether, about 0.83% w/v sodium phosphate monobasic monohydrate, about 0.17% w/v citric acid monohydrate, hydrochloric acid and/or sodium hydroxide, and water, and the composition can have a pH of about 5. The composition can include about 8000 ppm sodium chlorite, about 0.5% w/v poly(ethylene glycol)-block-poly(propylene glycol)-block-poly(ethylene glycol), about 0.83% w/v sodium phosphate monobasic monohydrate, about 0.17% w/v citric acid monohydrate, hydrochloric acid and/or sodium hydroxide, and water, and the composition can have a pH of about 5. The at least one buffer can be a phosphate buffer, a citrate buffer, or a borate buffer. The composition can have a pH less than or equal to 5.

In an interrelated aspect, disclosed are methods for treating ocular tissue with an antiseptic composition including sodium chlorite and a surfactant. Treating can include topically applying the antiseptic composition to an eye of a patient. Topically applying the antiseptic composition to the eye can include topically applying the antiseptic composition prior to, during, and/or after a surgical procedure.

In an interrelated aspect, disclosed is the ocular use of a composition including sodium chlorite and a surfactant. The sodium chlorite can be in an amount of about 800 ppm to about 8000 ppm. The surfactant can be in an amount of about 0.015% w/v to about 0.5% w/v. The composition can further include at least one buffer having a pH of less than or equal to 5. The composition can be topically applied to an eye tissue. The composition can be topically applied to an eye tissue prior to, during, and/or after a surgical procedure of an eye.

Other features and advantages will be apparent from the following description of various embodiment, which illustrate, by way of example, the principles of the disclosed compositions and methods.

DETAILED DESCRIPTION

Figure 1:
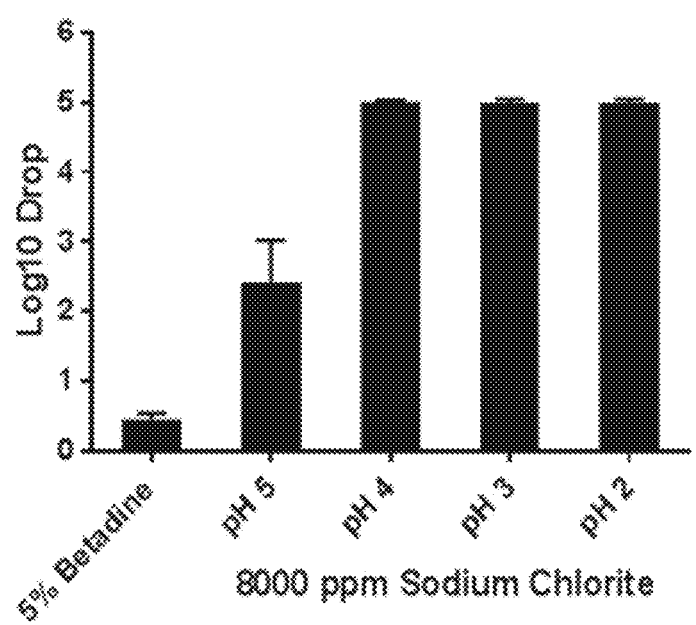
FIG. 1 shows the anti-microbial kill efficacies of sodium chlorite activated with buffers having different pH compared to 5% povidone-iodine ophthalmic solution.

There is a need for effective antiseptic and antimicrobial agents suitable for ophthalmic use. Sodium chlorite has been used as a preservative for ophthalmic formulations because they cause little to no irritation or damage to the eye. In addition to its known preservative utility, sodium chlorite is an effective antimicrobial agent. Certain sodium chlorite compositions, even at higher concentrations greater than when used in a preservative function, are surprisingly well-tolerated and cause little to no adverse events when administered.

Described herein are antiseptic compositions containing sodium chlorite activated in a buffer. The antiseptic compositions provide antimicrobial activity, in particular to eye tissues, with less ocular irritation and toxicity compared to povidone-iodine ophthalmic solutions. In some implementations, the compositions containing activated sodium chlorite include a surfactant and are up to 50,000 times more effective than povidone-iodine (Betadine®) as a rapid-onset anti-microbial agent without the ocular irritation and toxicity associated with povidone-iodine ophthalmic solution. In some implementations, the sodium chlorite is formulated at concentrations ≥800 ppm sodium chlorite, activated with buffers at pH ≤5, and include non-ionic surfactants (e.g. polyoxyethylene sorbitan monooleate (polysorbate-80 or PS-80), polyoxyethylene lauryl ether (Brij-35), or Pluronic F-127) at concentrations ranging from 0.05% to 0.5%. The anti-microbial efficacy of the sodium chlorite composition having PS-80 showed an unexpected efficacy over sodium chlorite compositions having other non-ionic surfactants.

"Antiseptic," as used herein, may be used to refer to a substance that can be used on living tissues for its antimicrobial activity. "Antimicrobial," as used herein, may be used to refer to a substance that kills or inhibits reproduction of pathogens, including but not limited to bacteria, viruses, fungi, protozoans, parasites, and so forth.

"Infection," as used herein, may be used to refer to an invasion of an organism's body tissues by a pathogen, any multiplication of the invading pathogen in a bodily tissue, and/or any toxins or reactions (including immunological reactions) caused by such invasion. Pathogens may include bacteria, viruses, fungi, protozoans, parasites, and so forth. Infections may occur in infection sites such as eyes; ears; nasal passages; the buccal or tracheal passages; skin sites including hands, fingers, feet, and toes; genitourinary passages including the vagina; the bladder; cuts, abrasions, lacerations, fistulae, pressure sores, ulcers, and the like.

As used herein, "sodium chlorite" refers to "stabilized chlorine dioxide," commercially available as Purite® (AGN-238749-Z), which is an aqueous solution of sodium chlorite ($NaClO_2$). U.S. Pat. No. 5,424,078, which is incorporated herein by reference in its entirety, further discusses the use of stabilized chlorine dioxide as a preservative for ophthalmic formulations. While stabilized chlorine dioxide has been used as a preservative for use in ophthalmic products, it has not been used as an antiseptic or a rapid-onset anti-microbial agent for antimicrobial preparation of a surgical site, as disclosed herein. Various implementations containing stabilized chlorine dioxide contemplated herein include all forms of sodium chlorite salts or solutions, as well as other chlorite salts and/or chlorite solutions not containing sodium (for example but without limitation, lithium, potassium, calcium, magnesium, zinc).

Chlorine dioxide ($ClO_2$) can be generated from sodium chlorite ($NaClO_2$) upon activation with a buffer. The generation of chlorine dioxide from sodium chlorite ($NaClO_2$) can be represented by the equation: $5\ NaClO_2 + 5\ H^+ \rightarrow [HClO_2] \rightarrow 4\ ClO_2 + 2\ H_2O + HCl + 5\ Na^+$. The sodium chlorite can be activated with a buffer having a pH less than or equal to pH 5, such as a pH2, pH3, pH4, or pH5. Sodium chlorite in the presence of a pH 5.0 activating buffer provides approximately 0.1% chlorine dioxide. Sodium chlorite in the presence of a pH 4.0 activating buffer provides approximately 1.0% chlorine dioxide (or 10× pH 5.0). The sodium chlorite concentrations may be described herein in ppm (parts per million). The source of sodium chlorite can be Purite®, which is typically provided as a 2.0% stock solution, where the percentage refers to the percent of potential chlorine dioxide generated from the sodium chlorite in the stock solution. Table 1 below provides an explanation for the conversion of % Purite®, where % w/v or ppm of Purite® represents the potential chlorine dioxide concentration achieved upon activation of the sodium chlorite contained in the Purite®. The % w/v (ppm) of sodium chlorite assumes a stoichiometric conversion (80% yield) of sodium chlorite into chlorine dioxide.

TABLE 1

| % Purite® (potential chlorine dioxide) | mM Purite® | % NaClO$_2$* | mM NaClO$_2$ |
|---|---|---|---|
| 2.0 (20,000 ppm) | 296 | 3.35 (33,500 ppm) | 370 |
| 1.0 (10,000 ppm) | 148 | 1.68 (16,800 ppm) | 185 |
| 0.5 (5,000 ppm) | 74 | 0.84 (8,400 ppm) | 93 |
| 0.1 (1,000 ppm) | 14.8 | 0.168 (1,680 ppm) | 18.35 |
| 0.05 (500 ppm) | 7.4 | 0.084 (840 ppm) | 9.3 |
| 0.01 (100 ppm) | 1.48 | 0.0168 (168 ppm) | 1.85 |
| 0.005 (50 ppm) | 0.74 | 0.0084 (84 ppm) | 0.93 |
| 0.0001 (1 ppm) | 0.0148 | 0.000168 (1.68 ppm) | 0.0186 |

*Assumes a stoichiometric conversion (80% yield) of sodium chlorite into chlorine dioxide.

In some implementations, the composition contains at least about 0.08% w/v sodium chlorite or about 800 ppm sodium chlorite up to about 0.8% w/v sodium chlorite or about 8000 ppm sodium chlorite). In other implementations, the sodium chlorite concentrations in the compositions include 0.08% w/v, 0.085% w/v, 0.09% w/v, 0.095% w/v, 0.10% w/v, 0.15% w/v, 0.30% w/v, 0.35% w/v, 0.40% w/v, 0.45% w/v, 0.50% w/v, 0.55% w/v, 0.60% w/v, 0.65% w/v, 0.70% w/v, 0.75% w/v, 0.80% w/v, and 0.85% w/v, and may all be used in conjunction with the implementations described herein. In some implementations, the composition contains at least about 0.05% w/v Purite® or about 500 ppm Purite® up to about 0.5% w/v Purite® or about 5000 ppm Purite®), wherein the % w/v or ppm represents potential chlorine dioxide upon activation of the sodium chlorite in the Purite®. In other implementations, the Purite® concentrations in the composition include 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.10% w/v, 0.15% w/v, 0.20% w/v, 0.25% w/v, 0.30% w/v, 0.35% w/v, 0.40% w/v, 0.45% w/v, 0.50% w/v, and may all be used in conjunction with the implementations described herein.

In some implementations, the sodium chlorite is activated by one or more activating buffers. Example buffers considered herein include, but are not limited to, acetate buffers, citrate buffers, phosphate buffers, borate buffers, lactate buffers, NaOH/trolamine buffers, or a combination thereof, such as phosphate and citrate or borate and citrate. In some implementations the buffer is sodium phosphate monobasic monohydrate and citric acid monohydrate (see Table 2). In other implementations, the buffer is sodium borate, decahydrate. Acids or bases, such as HCl and NaOH, may be used to adjust the pH as needed. The activating buffer can have a pH 2, pH 3, pH 4, pH 5, pH 6, or pH 7. In other implementations, the pH of the activating buffer can be less than or equal to pH 5. In other implementation, the pH of the activating buffer can be up to about pH 7.6. The amount of buffer used may vary. In some embodiments, the buffer may have a concentration in a range of about 1 nM to about 100 mM.

TABLE 2

Buffer composition for sodium chlorite activation

| Buffer Ingredients | Buffer for pH 2 | Buffer for pH 3 | Buffer for pH 4 | Buffer for pH 5 |
|---|---|---|---|---|
| | % w/v | | | |
| Sodium Phosphate Monobasic Monohydrate | 0.15 | 0.15 | 0.25 | 0.83 |
| Citric Acid Monohydrate | 1.0 | 1.0 | 0.35 | 0.17 |
| Hydrochloric acid 1N | 6 | 0 | 0 | 0 |
| Sodium Hydroxide 1N | 0 | 0 | 0 | 0.92 |

The composition can further include one or more co-solubilizers such as a surfactant. The surfactant may vary, and may include any compound that is surface active or can form micelles. A surfactant may be used for assisting in dissolving an excipient or an active agent, dispersing a solid or liquid in a composition, enhancing wetting, modifying drop size, stabilizing an emulsion, or a number of other purposes. Examples of surfactants may include, but are not limited to, surfactants of the following classes: alcohols, for example polyvinyl alcohol; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal & veg.); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants such as Soluplus® (from BASF); propoxylated & ethoxylated fatty acids, alcohols, or alkyl phenols; protein-based surfactants; sarcosine derivatives; sorbitan derivatives; sucrose and glucose esters and derivatives; and saponins. In some embodiments, the surfactant may include polyethylene glycol (15)-hydroxystearate (CAS Number 70142-34-6, available as SOLUTOL HS 15® from BASF), a polyoxyethylene-polyoxypropylene block copolymer (CAS No. 9003-11-6, available as PLURONIC® F-68 from BASF), polyoxyethylene 40 stearate (POE40 stearate), polysorbate 80 or polyoxyethylene (80) sorbitan monooleate (CAS No. 9005-65-6), sorbitan monostearate (CAS No. 1338-41-6, available as SPAN™ 60 from Croda International PLC), or polyoxyethyleneglyceroltriricinoleate 35 (CAS No. 61791-12-6, available as CREMOPHOR EL® from BASF), ethoxylated castor oil, such as Cremophor EL (CAS Number 61791-12-6). Suitable co-solubilizers include, but are not limited to, povidone, and acrylates (e.g. PEMULEN®).

In some implementations, the surfactant is a non-ionic surfactant that can preferably include polyoxyethylene sorbitan monooleate (Polysorbate-80) represented by CAS No. 9005-65-6, such as Tween® 80, available from Sigma- Aldrich. In some implementations, the non-ionic surfactant includes polyoxyethylene lauryl ether represented by CAS No. 9002-92-0, such as Brij® 35, available from Sigma-Aldrich. In some implementations, the non-ionic surfactant polyol includes poly(ethylene glycol)-block-poly(propylene glycol)-block-poly(ethylene glycol) represented by CAS No. 9003-11-6, such as Pluronic™ F-127, available from BASF SE. Other non-ionic surfactants are considered herein including, but not limited to ethoxylates, fatty alcohol ethoxylates, alkylphenol ethoxylates, fatty acid ethoxylates, special ethoxylated fatty esters and oils, ethoxylated amines and/or fatty acid amides, terminally blocked ethoxylates, fatty acid esters of polyhydroxy compounds, fatty acid esters of glycerol, fatty acid esters of sorbitol, Tweens, fatty acid esters of sucrose, alkyl polyglucosides, amine oxides, sulfoxides, phosphine oxides.

It should be appreciated that the surfactant incorporated in the compositions is not limited by class and that various classes of surfactants can be incorporated including, but not limited to anionic, cationic, zwitterionic, and nonionic surfactants. It should also be appreciated combinations of surfactants can be included.

The amount of surfactant may vary. In some implementations, the surfactant can be used at a concentration from about 0.005% w/v to about 5.0% w/v, preferably 0.015% w/v to about 0.5% w/vv. Some preferred concentrations of the surfactant include 0.005% w/v, 0.006% w/v, 0.006% w/v, 0.007% w/v, 0.008% w/v, 0.009% w/v, 0.010% w/v, 0.011% w/v, 0.012% w/v, 0.013% w/v, 0.014% w/v, 0.015% w/v, 0.016% w/v, 0.017% w/v, 0.018% w/v, 0.019% w/v, 0.020%. 0.025%, 0.030%, 0.035%, 0.04% w/v, 0.045% w/v, 0.05% w/v, 0.055% w/v, 0.06% w/v, 0.065% w/v, 0.07% w/v, 0.075% w/v, 0.08% w/v, 0.085% w/v, 0.09% w/v, 0.095% w/v, 0.10% w/v, 0.15% w/v, 0.20% w/v, 0.25% w/v, 0.30% w/v, 0.35% w/v, 0.40% w/v, 0.45% w/v, 0.50% w/v, 0.55% w/v, 0.60% w/v, 0.65% w/v, 0.70% w/v, 0.75% w/v, 0.80% w/v, 0.85% w/v, 0.90% w/v, 0.95% w/v, 1.0% w/v, 1.5% w/v, 2.0% w/v, 2.5% w/v, 3.0% w/v, 3.5% w/v, 4.0% w/v, 4.5% w/v, and 5.0% w/v and may all be used in conjunction with the implementations described herein.

In some implementations, the composition can include ≥800 ppm sodium chlorite activated in an activating buffer having a pH ≤5, and added polysorbate 80 at a concentration between about 0.25% up to about 0.5%. Table 3 provides various compositions of sodium chlorite containing polysorbate 80 (PS80).

TABLE 3

| Sodium Chlorite (ppm) | pH of activating buffer | PS80 (% w/v) |
|---|---|---|
| 800 | 4 | 0.25 |
| 1000 | 4 | 0.25 |
| 2000 | 4 | 0.25 |
| 3000 | 4 | 0.25 |
| 4000 | 4 | 0.25 |
| 5000 | 4 | 0.25 |
| 6000 | 4 | 0.25 |
| 7000 | 4 | 0.25 |
| 8000 | 4 | 0.25 |
| 800 | 5 | 0.25 |
| 1000 | 5 | 0.25 |
| 2000 | 5 | 0.25 |
| 3000 | 5 | 0.25 |
| 4000 | 5 | 0.25 |
| 5000 | 5 | 0.25 |
| 6000 | 5 | 0.25 |
| 7000 | 5 | 0.25 |
| 8000 | 5 | 0.25 |
| 800 | 4 | 0.5 |
| 1000 | 4 | 0.5 |
| 2000 | 4 | 0.5 |
| 3000 | 4 | 0.5 |
| 4000 | 4 | 0.5 |
| 5000 | 4 | 0.5 |
| 6000 | 4 | 0.5 |
| 7000 | 4 | 0.5 |
| 8000 | 4 | 0.5 |
| 800 | 5 | 0.5 |
| 1000 | 5 | 0.5 |
| 2000 | 5 | 0.5 |
| 3000 | 5 | 0.5 |
| 4000 | 5 | 0.5 |
| 5000 | 5 | 0.5 |
| 6000 | 5 | 0.5 |
| 7000 | 5 | 0.5 |
| 8000 | 5 | 0.5 |

In some implementations, the activated sodium chlorite compositions may be prepared in the form of a solution, for example a solution using a physiological saline solution as a major vehicle. Solutions may be maintained at a comfortable pH with an appropriate buffer system. The formulations may also contain conventional, pharmaceutically acceptable preservatives, stabilizers and surfactants. In a preferred implementation, the composition is formulated as an ophthalmically acceptable liquid or solution.

Certain liquid compositions may include an osmolality agent. The osmolality agent may vary, and may include any compound or substance useful for adjusting the osmolality of a liquid. Examples include, but are not limited to, salts, particularly sodium chloride or potassium chloride, organic compounds such as propylene glycol, mannitol, or glycerin, or any other suitable osmolality adjustor. In some embodiments, an osmolality agent may comprise propylene glycol, glycerin, mannitol, sodium chloride, or a combination thereof. The amount of osmolality agent may vary depending upon whether an isotonic, hypertonic, or hypotonic liquid is desired. In some embodiments, the amount of an osmolality agent such as those listed above may be at least about 0.0001% w/w up to about 1% w/w, about 2% w/w, or about 5% w/w.

As described above, the sodium chlorite can be activated in a buffer generating chlorine dioxide prior to formulation of the final composition to be applied to the eye, skin, or other target treatment area. In some implementations, the activating buffer can be a citrate or phosphate buffer considered suitable for lower pH solutions. In other implementations, the activating buffer can be a borate buffer considered suitable for higher pH solutions (e.g. in the pH 7 range). The citrate and phosphate activating buffers can be sufficient to achieve desired final isotonicity of the final ophthalmic solution from these relatively low pH solutions. The borate buffers, in contrast, may include additional osmolality agents, such as glycerol, to achieve desired final isotonicity.

In some embodiments, an additional co-solubilizer may comprise sorbitan monostearate, a polyoxyethylene-polyoxypropylene block copolymer, polyoxyethyleneglycerol-triricinoleate 35, a cyclodextrin, or a combination thereof. Certain compositions may include an antioxidant. The antioxidant may vary, and may include any compound or substance that is useful in reducing oxidation of any compound present in the composition. Examples include, but are not limited to, citrate, L-carnosine, oleic acid, and zinc.

Certain compositions may include a chelating agent. The chelating agent may vary, and may include any compound or substance that is capable of chelating a metal. A useful chelating agent is edetate disodium, although other chelating agents may also be used in place or in conjunction with it.

In some embodiments, compositions may include one or more viscosity enhancers. For example, a viscosity enhancer may comprise an acrylic acid or acrylate polymer, either cross-linked or non-cross-linked such as polycarbophil, for example CARBOPOL® (B.F. Goodrich, Cleveland, Ohio) and CARBOPOL 980®. These polymers may dissolve in water and may form a clear or slightly hazy gel upon neutralization with a base such as sodium hydroxide, potassium hydroxide, triethanolamine, or other amine bases. Other commercially available thickeners may include HYPAN® (Kingston Technologies, Dayton, N.J.), NATROSOL® (Aqualon, Wilmington, Del.), KLUCEL® (Aqualon, Wilmington, Del.), or STABILEZE® (ISP Technologies, Wayne, N.J.). KLUCEL® is a cellulose polymer that may be dispersed in water and may form a uniform gel upon complete hydration. Other useful gelling polymers may include carboxymethyl cellulose, hydroxyethyl cellulose, hydroxypropylcellulose, cellulose gum, MVA/MA copolymers, MVE/MA decadiene crosspolymer, PVM/MA copolymer, etc.

In some implementations, the composition preferably takes the form of an aqueous solution configured to be applied as a drop, wash, swab, or bath. Other suitable forms are emulsions (oil-in-water or water-in-oil), lotions, creams, ointments, salves, gels, instillations, foams, powders, tinctures, solids, and so forth. Preferably, the composition is configured to be administered topically to a body surface, which may include sites such as the eye, skin, mucous membranes, incision site, wound location, or other treatment site.

In some implementations, the composition can be provided as part of a kit where the final composition is mixed together by an end user prior to use. For example, a first formulated part (e.g. a buffer solution with or without one or more other excipients such as a surfactant mixed to a desired concentration, tonicity agent, etc.) can be provided in a first container and a second formulated part (e.g. a sodium chlorite stock solution) provided in a second container. The two formulated parts can be mixed together to form the final composition (e.g. as a 1:1, 1:2, 1:3, or other mixture). The two parts can be mixed together before being dispensed.

The compositions described herein can have enhanced bacterial kill efficacy compared to povidone-iodine (i.e. Betadine®) without the associated ocular toxicity. Thus, the compositions described herein can be used similarly to how povidone-iodine is currently used with greater efficacy in anti-microbial kill and with little to no toxicity to the ocular tissue. The compositions described herein are preferably prophylactic in their use, prior to exposure to a pathogen capable of causing an infection or prior to the establishment of an infection. In some implementations, the composition can be administered to a treatment site as a single, one-time application sufficient to disinfect and prepare the treatment site for a surgical procedure. The compositions described herein are useful as an antimicrobial preparation for all ocular procedures, for example, invasive procedures including intraocular injections, including intraviteal, intracorneal, scleral, sub-Tenon's, or sub-conjunctival injections, as well as various ocular surgical procedures, including cataract, trabeculectomy, etc. Thus, the compositions can be formulated as an eye drop, eye wash, eye swab, or an eye bath for use on eye lids, eye brow, cheek, cornea, conjunctiva, palpebral fornices, etc.

Although the compositions are described herein as preferably configured for ocular applications, they should not be limited as such. The compositions described herein can be applied topically to a variety of body surfaces, including the eye, ear, skin, nails, or mucous membranes. The compositions can be useful in non-ocular skin applications, including applications where a biofilm can present bacteria prior to a surgery where a robust bacterial kill is desired, for example, implant surgeries characterized by creating pockets in tissues that are washed out with antiseptics prior to positioning an implant (e.g. breast implant surgery) It will be noted that while some implementations described herein may be suitable as a prophylactic agent, the implementations are not limited as such. The compositions can be used for the treatment (e.g. cleansing) of an existing wound or surgical incision site (e.g. ocular or non-ocular site). The compositions can be administered at least once a day to a treatment site, although some implementations may permit a single, one-time dosage sufficient to treat the wound. In some implementations, treatment may be administered to a treatment site at least once a week. Some implementations may provide for more frequent dosing, for example once daily, twice daily, three times daily, four times daily, six times daily, or eight times daily. The implementations described herein may also be usable in a veterinary context, and not only for the treatment of humans.

Tables 4-7 below lists various examples of compositions considered herein that are ophthalmically acceptable topical antiseptics for ocular tissues.

TABLE 4

| Part A Composition (2% Purite stock) | |
|---|---|
| Sodium chlorite | 36.85 mg/mL |
| Sodium chloride | 2.75 mg/mL |
| Sodium hydrogen carbonate | 2 mg/mL |
| Sodium formate | 0.94 mg/mL |
| Methanol | 0.5 mg/mL |
| Sodium chlorate | 0.16 mg/mL |
| Water | 956 mg/mL |
| Part B Composition (Buffer Solution) | |
| Polysorbate 80 | 0.50% w/v |
| Sodium phosphate monobasic monohydrate | 0.83% w/v |
| Citric acid monohydrate | 0.17% w/v |
| Sodium hydroxide 1N | pH adjust |
| Final pH after A:B reconstitution | 5 |

TABLE 5

| Part A Composition (2% Purite stock) | |
|---|---|
| Sodium chlorite | 36.85 mg/mL |
| Sodium chloride | 2.75 mg/mL |
| Sodium hydrogen carbonate | 2 mg/mL |
| Sodium formate | 0.94 mg/mL |
| Methanol | 0.5 mg/mL |
| Sodium chlorate | 0.16 mg/mL |
| Water | 956 mg/mL |
| Part B Composition (Buffer Solution) | |
| Polysorbate 80 | 0.50% w/v |
| Sodium phosphate monobasic monohydrate | 0.25% w/v |
| Citric acid monohydrate | 0.35% w/v |
| Final pH after A:B reconstitution | 4 |

TABLE 6

| Part A Composition (2% Purite stock) | |
|---|---|
| Sodium chlorite | 36.85 mg/mL |
| Sodium chloride | 2.75 mg/mL |
| Sodium hydrogen carbonate | 2 mg/mL |
| Sodium formate | 0.94 mg/mL |
| Methanol | 0.5 mg/mL |
| Sodium chlorate | 0.16 mg/mL |
| Water | 956 mg/mL |
| Part B Composition (Buffer Solution) | |
| Polysorbate 80 | 0.50% w/v |
| Sodium phosphate monobasic monohydrate | 0.15% w/v |
| Citric acid monohydrate | 1.0% w/v |
| Final pH after A:B reconstitution | 3 |

TABLE 7

| Part A Composition (2% Purite ® stock) | |
|---|---|
| Sodium chlorite | 36.85 mg/mL |
| Sodium chloride | 2.75 mg/mL |
| Sodium hydrogen carbonate | 2 mg/mL |
| Sodium formate | 0.94 mg/mL |
| Methanol | 0.5 mg/mL |
| Sodium chlorate | 0.16 mg/mL |
| Water | 956 mg/mL |
| Part B Composition (Buffer Solution) | |
| Polysorbate 80 | 0.5% w/v |
| Sodium phosphate monobasic monohydrate | 0.15% w/v |
| Citric acid monohydrate | 1.0% w/v |
| Hydrochloric acid 1N | pH adjust |
| Final pH after A:B reconstitution | 2 |

Table 8 below lists various examples of compositions considered herein that are ophthalmically acceptable topical antiseptics for ocular tissues.

TABLE 8

| Composition 1 | |
|---|---|
| Sodium chlorite | 8000 ppm |
| Polysorbate 80 | 0.015% w/v |
| Sodium phosphate monobasic monohydrate | 0.25% w/v |
| Citric acid monohydrate | 0.35% w/v |
| pH | 4 |
| Composition 2 | |
| Sodium chlorite | 8000 ppm |
| Polysorbate 80 | 0.25% w/v |
| Sodium phosphate monobasic monohydrate | 0.25% w/v |
| Citric acid monohydrate | 0.35% w/v |
| pH | 4 |
| Composition 3 | |
| Sodium chlorite | 8000 ppm |
| Polysorbate 80 | 0.50% w/v |
| Sodium phosphate monobasic monohydrate | 0.25% w/v |
| Citric acid monohydrate | 0.35% w/v |
| pH | 4 |
| Composition 4 | |
| Sodium chlorite | 800 ppm |
| Polysorbate 80 | 0.50% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 5 | |
| Sodium chlorite | 1600 ppm |
| Polysorbate 80 | 0.50% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 6 | |
| Sodium chlorite | 3200 ppm |
| Polysorbate 80 | 0.50% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 7 | |
| Sodium chlorite | 4800 ppm |
| Polysorbate 80 | 0.50% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 8 | |
| Sodium chlorite | 6400 ppm |
| Polysorbate 80 | 0.50% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 9 | |
| Sodium chlorite | 8000 ppm |
| Sodium phosphate monobasic monohydrate | 0.83% w/v |
| Citric acid monohydrate | 0.17% w/v |
| Sodium Hydroxide 1N | pH adjust |
| pH | 5 |
| Composition 10 | |
| Sodium chlorite | 8000 ppm |
| Sodium phosphate monobasic monohydrate | 0.25% w/v |
| Citric acid monohydrate | 0.35% w/v |
| pH | 4 |
| Composition 11 | |
| Sodium chlorite | 8000 ppm |
| Sodium phosphate monobasic monohydrate | 0.15% w/v |
| Citric acid monohydrate | 1.0% w/v |
| pH | 3 |
| Composition 12 | |
| Sodium chlorite | 8000 ppm |
| Sodium phosphate monobasic monohydrate | 0.15% w/v |
| Citric acid monohydrate | 1.0% w/v |
| Hydrochloric acid 1N | pH adjust |
| pH | 2 |
| Composition 13 | |
| Sodium chlorite | 8000 ppm |
| Polysorbate 80 | 0.50% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 14 | |
| Sodium chlorite | 8000 ppm |
| Brij 35 | 0.015% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 15 | |
| Sodium chlorite | 8000 ppm |
| Brij 35 | 0.25% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 16 | |
| Sodium chlorite | 8000 ppm |
| Brij 35 | 0.50% w/v |

TABLE 8-continued

| | |
|---|---|
| Sodium phosphate monobasic monohydrate | 0.83% w/v |
| Citric acid monohydrate | 0.17% w/v |
| Sodium Hydroxide 1N | pH adjust |
| pH | 5 |
| Composition 17 | |
| Sodium chlorite | 8000 ppm |
| PF127 | 0.015% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 18 | |
| Sodium chlorite | 8000 ppm |
| PF127 | 0.25% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 19 | |
| Sodium chlorite | 8000 ppm |
| PF127 | 0.50% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 20 | |
| Sodium chlorite | 8000 ppm |
| Saponin | 0.015% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 21 | |
| Sodium chlorite | 8000 ppm |
| Saponin | 0.25% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 22 | |
| Sodium chlorite | 8000 ppm |
| Saponin | 0.50% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 23 | |
| Sodium chlorite | 8000 ppm |
| CMC | 0.015% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 24 | |
| Sodium chlorite | 8000 ppm |
| CMC | 0.25% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 25 | |
| Sodium chlorite | 8000 ppm |
| CMC | 0.50% w/v |
| Sodium phosphate monobasic monohydrate | 0.83% w/v |
| Citric acid monohydrate | 0.17% w/v |
| Sodium Hydroxide 1N | pH adjust |
| pH | 5 |
| Composition 26 | |
| Sodium chlorite | 1600 ppm |
| Sodium borate decahydrate | 0.6% w/v |
| Sodium citrate monohydrate | 0.1% w/v |
| pH | 7.6 |

Example 1

Anti-Microbial Kill Efficacies of Sodium Chlorite Compositions Compared to 5% Povidone-Iodine Time kill efficacy experiments were performed against *Staphylococcus aureus* ATCC 29213 (*S aureus*). Plates with Tryptic Soy agar (TSA) were inoculated with cultures of *S aureus* and incubated at 30-35° C. for 24 hours. Bacterial cultures were harvested and sample suspensions were adjusted to contain approximately $10^5$-$10^6$ colony-forming units (CFU) per milliliter. For each test, 10 mL of the test article (Betadine® 5% Sterile Ophthalmic Prep Solution (povidone-iodine ophthalmic solution; Alcon, Fort Worth, Tex.) or sodium chlorite) with or without surfactant was dispensed into sterile glass test tubes, inoculated with 100 µL of *S aureus* suspension and mixed thoroughly. Sodium chlorite was activated with one of four buffers varying in their pH (pH 5, pH 4, pH 3, or pH 2) for 30 seconds up to 5 minutes and then dispensed. After 30 seconds of exposure, 1 mL of the test suspension was removed and added to 9.0 mL of Dey-Engley neutralizer. One hundred µL of this neutralized suspension was plated in triplicates on TSA plates using an automated spiral plating instrument (Eddyjet 2, Neutec group Inc, New York, USA), with 7 log serial dilution mode. All bacterial plates were incubated at 30-35° C. for 2 days. The log drop values are determined as the difference between the logged CFU in the plates with and without the test article.

FIG. 1 shows the anti-microbial kill efficacies of 8000 ppm formulations of sodium chlorite activated with buffers having different pH compared to 5% povidone-iodine solution. n=3 per formulation and error bars represent SD. The log reductions of sodium chlorite activated with buffers having pH 5, pH 4, pH 3, and pH 2 were 2.4, 5.0, 5.0 and 5.0, respectively. Each of these log reductions were significantly higher than the log reduction achieved with 5% povidone-iodine solution, which was 0.46 (p<0.001, ANOVA, Dunnet's multiple comparisons). In addition, sodium chlorite activated with pH 4, pH 3, and pH 2 buffers had a significantly higher kill efficacy than sodium chlorite activated with pH 5 buffer (p<0.001, ANOVA, Dunnet's multiple comparisons). The bacterial log reductions increased with decreasing pH values.

Figure 2:
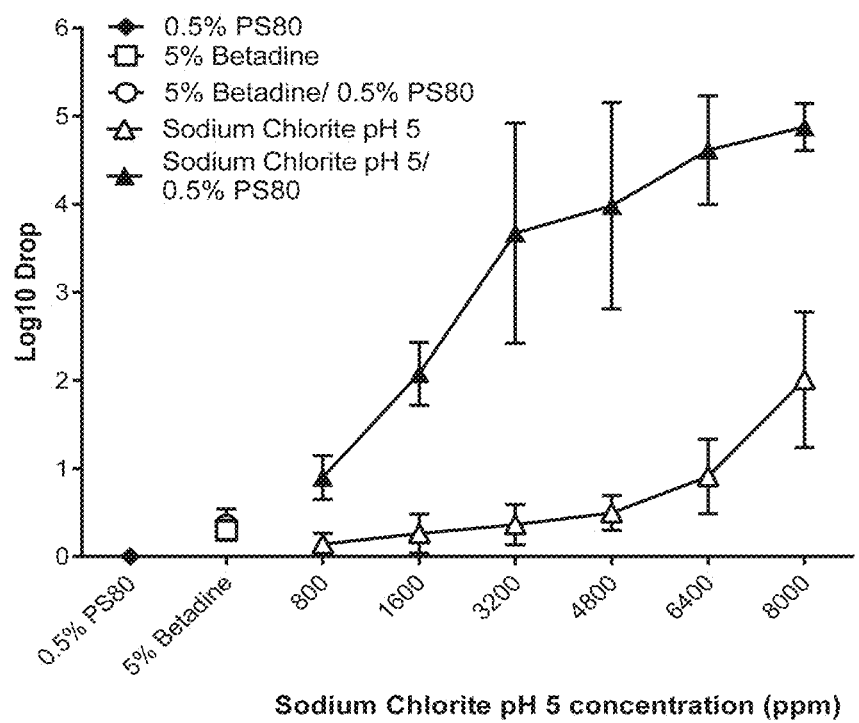
FIG. 2 shows the concentration response curves of sodium chlorite activated with pH 5 buffer in the presence and absence of 0.5% polysorbate 80.

FIG. 2 shows the concentration-response curves of sodium chlorite activated with pH 5 buffer in the presence and absence of a surfactant, 0.5% polysorbate 80. The anti-microbial kill efficacy of sodium chlorite was tested for concentrations 800 ppm-8000 ppm, each activated with pH 5 buffer and in the presence and absence of the non-ionic surfactant, 0.5% polysorbate 80 (PS80). N=3 per formulation and error bars represent SD. The kill efficacy increased as a function of sodium chlorite concentrations in the presence and in the absence of the PS80. Without PS80 (open triangles), the 4800 ppm and 6400 ppm concentrations of sodium chlorite were more efficacious than 5% povidone-iodine (open squares). With PS80 (closed triangles), the 800 ppm-8000 ppm sodium chlorite concentrations were all more efficacious than sodium chlorite-only formulations (open triangles) and more efficacious than 5% povidone-iodine (open squares) (p<0.001, two-way ANOVA, Bonferroni multiple comparisons). PS80 (0.5%) did not have any effect on the kill efficacy of 5% povidone-iodine (p=0.44, paired student's t test), nor was it effective by itself.

Figure 3:
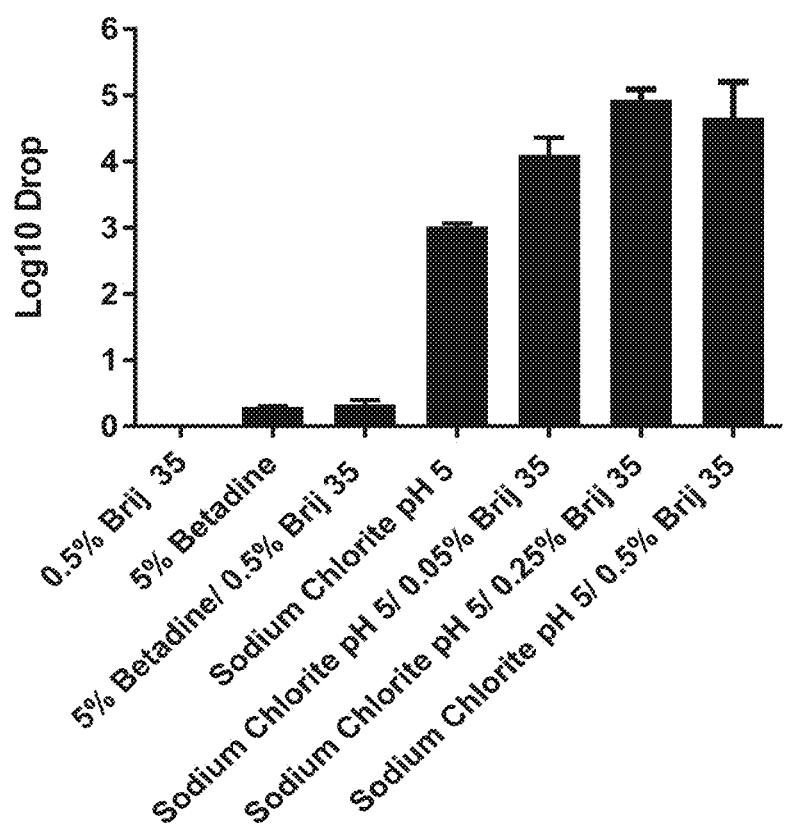
FIG. 3 shows the enhanced anti-microbial kill efficacy of sodium chlorite activated with pH 5 buffer in the presence of Brij 35.

FIG. 3 shows the enhanced anti-microbial kill efficacy of sodium chlorite concentrations at 8000 ppm in the presence of another non-ionic surfactant, Brij 35 (0.05%-0.5%). Brij 35 was tested for increased efficacy against *S aureus* when added to 5% povidone-iodine or 8000 ppm sodium chlorite activated with pH 5 buffer. N=2 per formulation and error bars represent SD. Brij 35 at the highest concentration tested (0.5%) did not have any efficacy by itself, nor did it enhance the efficacy of 5% povidone-iodine. By contrast, Brij 35 having concentrations between 0.05%-0.5% enhanced the efficacy of 8000 ppm sodium chlorite pH 5.

Figure 4:
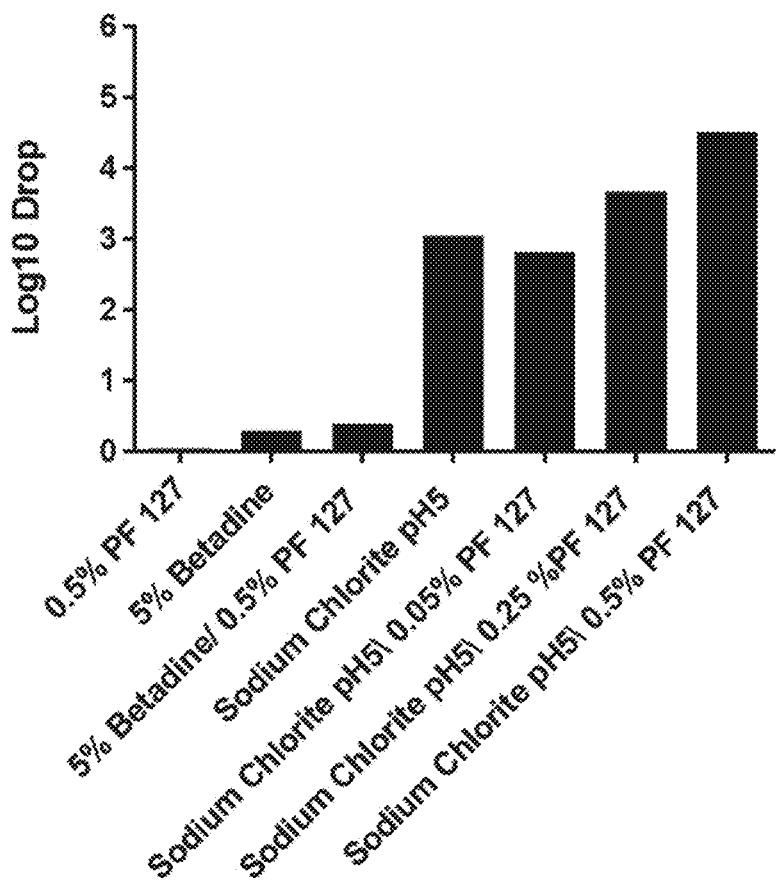
FIG. 4 shows the anti-microbial kill efficacy of sodium chlorite activated with pH 5 buffer in the presence of Pluronic F-127.

FIG. 4 shows the anti-microbial kill efficacy of sodium chlorite at 8000 ppm concentration in the presence of another non-ionic surfactant, Pluronic F-127 (0.05%-0.5%). Pluronic F-127 was tested for increased efficacy against *S aureus* when added to 5% povidone-iodine or 8000 ppm sodium chlorite activated with pH 5 buffer. N=1 per formulation. Similar to what is described above for Brij 35, Pluronic F-127 at the highest concentration tested (0.5%) did not have any efficacy by itself, nor did it enhance the efficacy of 5% povidone-iodine. Pluronic F-127 at 0.25% and 0.5% both appeared to augment the efficacy of 8000 ppm sodium chlorite pH 5.

Figure 5A:
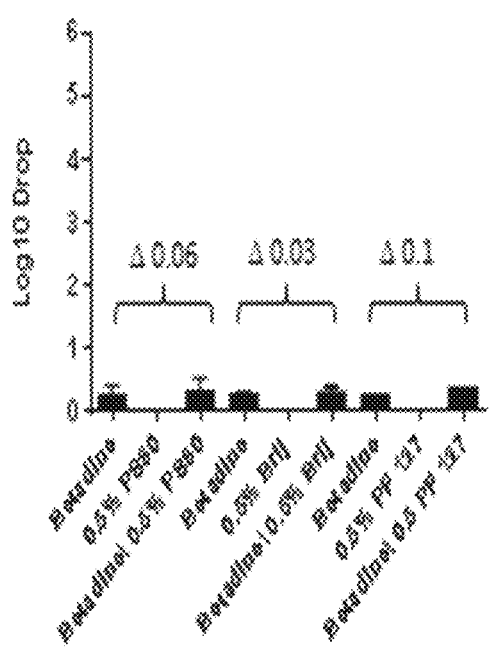
FIG. 5A shows the effects of different surfactants on the kill efficacy of 5% povidone-iodine ophthalmic solution.
Figure 5B:
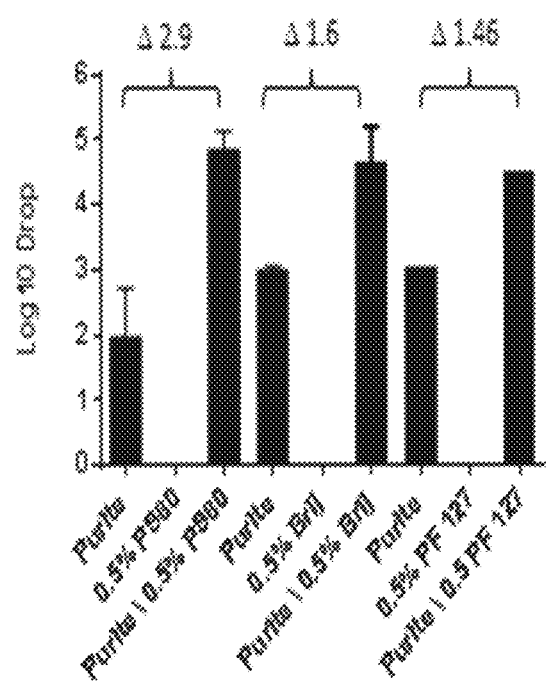
FIG. 5B shows the effects of different surfactants on the kill efficacy of 8000 ppm sodium chlorite activated with pH 5 buffer.

FIGS. 5A-5B compares the effects of the different surfactants on the kill efficacy of 5% povidone-iodine or 8000 ppm sodium chlorite activated at pH 5. The log reductions of 5% povidone-iodine alone were less than 0.5 (FIG. 5A). As discussed above, the surfactants alone did not have any efficacy by themselves, nor did they enhance the efficacy of 5% povidone-iodine (0.5% polysorbate 80 ($\Delta$ 0.06), 0.5% Brij 35 ($\Delta$ 0.03), or 0.5% Pluronic F-127 ($\Delta$ 0.1)). The log reductions achieved by 8000 ppm sodium chlorite alone were between about 2.0-3.0 (FIG. 5B). The efficacy of 8000 ppm sodium chlorite was significantly greater in the presence of 0.5% polysorbate 80 ($\Delta$ 2.9), 0.5% Brij 35 ($\Delta$ 1.6), or 0.5% Pluronic F-127 ($\Delta$ 1.46) compared to sodium chlorite alone. Additionally, the efficacy of 8000 ppm sodium chlorite was also significantly greater in the presence of 0.5% polysorbate 80 compared to the sodium chlorite formulations containing 0.5% Brij 35 or 0.5% Pluronic F-127.

Figure 6:
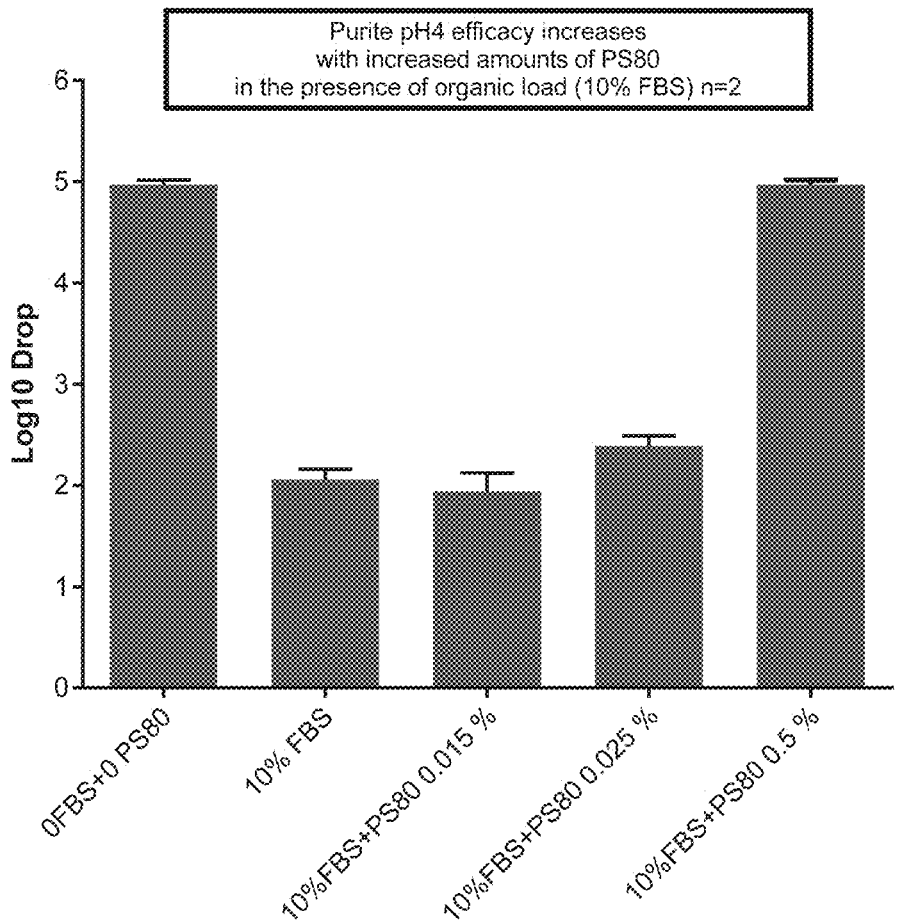
FIG. 6 shows the concentration response of polysorbate 80 on the kill efficacy of 8000 ppm sodium chlorite activated with pH 4 buffer in the presence of organic load.

FIG. 6 shows the concentration response of a surfactant (polysorbate 80) on the kill efficacy of 8000 ppm Sodium chlorite activated with pH 4 buffer in the presence of organic load simulated by 10% fetal bovine serum (FBS). In the absence of both 10% FBS and polysorbate 80 (PS80), sodium chlorite achieved a log reduction of about 5. The efficacy of sodium chlorite was reduced in the presence of 10% FBS from a log reduction of about 5 to about 2. The bactericidal effectiveness of sodium chlorite in the presence of 10% FBS was not significantly affected by the addition of PS80 at lower concentrations of 0.015% or 0.025%. However, 0.5% PS80 significantly increased the log reduction achieved by 8000 ppm sodium chlorite pH4. The log reduction achieved by sodium chlorite and 0.5% PS80 was essentially unaffected by the presence of the presence of FBS.

Example 2

Ocular Safety and Tolerability of Sodium Chlorite Compositions Compared to 5% Povidone-Iodine Ocular safety and tolerability experiments were conducted in non-sedated rabbits and included 1) an evaluation of corneal staining with topical sodium fluorescein, which is a readout of epithelial cell integrity, 2) an evaluation of ocular surface hyperemia, which is a readout of irritation, and 3) an evaluation of visual acuity, which is a readout of the degree to which visual performance is affected by damage to the cornea.

Corneal epithelial integrity was assessed as per NEI corneal staining guidelines for dry eyes (Lemp M A. Report of the National Eye Institute/Industry workshop on Clinical Trials in Dry Eyes. *CLAO J.* 1995; 21: 221-232). Rabbits were divided into 4 treatment groups: 5% povidone-iodine (n=8), sodium chlorite 8000 ppm formulations pH 3 (n=8), pH 4 (n=8) and pH 5 (n=4), and were unilaterally treated with a drop of proparacaine hydrochloride 0.5% for topical anesthesia prior to dosing with 250 ul of test formulation. Sodium chlorite was activated with buffers 5 minutes prior to dosing. Sodium chlorite was not washed out of the eye after dosing. Povidone-iodine was washed out using several sterile saline flushes 2 minutes after dosing as per label. A wet fluorescein strip containing 0.6 mg of dye (Ful-Glo strip; Akorn Pharmaceuticals, Inc., Buffalo Grove, Ill.) was applied to the inferior fornix and the cornea was photographed under a cobalt blue light source (BQ900; Haag Streit, Köniz, Switzerland) at 16× magnification. Fluorescein staining was graded based on NEI guidelines. Briefly, the cornea was divided into 5 regions (center, superior, temporal, nasal and inferior). Punctate staining in these regions were graded from 0 to 3 (0=0-5, 1=5-20, 2=20-50, 3=>50) and the mean of the grades from all the regions were reported.

Figure 7:
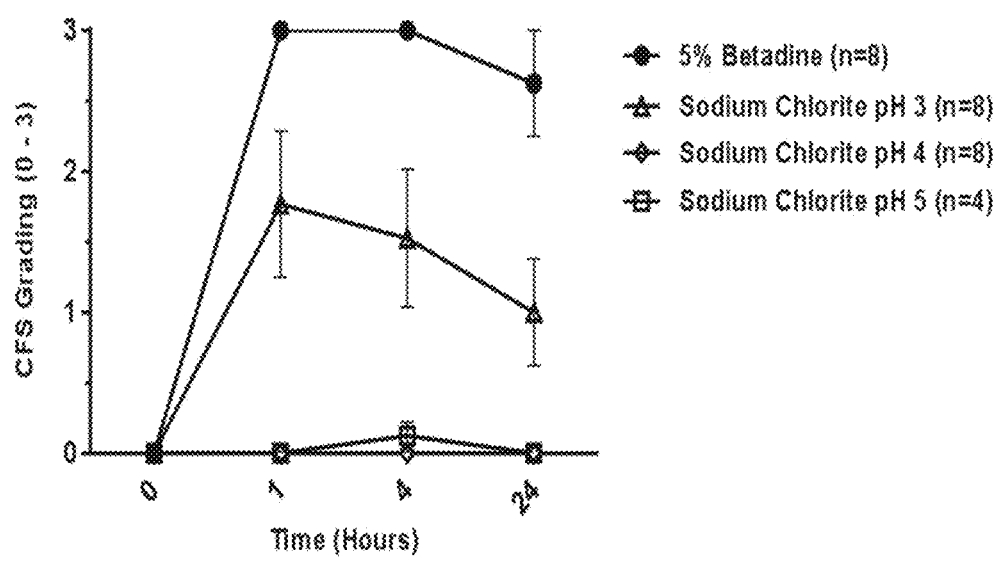
FIG. 7 shows in vivo corneal epithelial integrity of sodium chlorite activated with buffers having different pH compared to 5% povidone-iodine ophthalmic solution.

FIG. 7 shows in vivo corneal epithelial integrity of sodium chlorite activated with buffers having different pH compared to 5% povidone-iodine. FIG. 7 shows that 5% povidone-iodine had the maximum punctate staining that remained for 24 hours (2.6±1.1) followed by sodium chlorite activated with pH 3 buffer (1.0±1.1). Sodium chlorite formulations activated with pH 4 and pH 5 buffers did not show any corneal staining at 24 hrs. This shows that sodium chlorite formulations at pH 4 and pH 5 were well tolerated compared with 5% povidone-iodine and were not disruptive to the corneal epithelium.

Ocular surface hyperemia is another indication of eye irritation and ocular discomfort. Ocular surface hyperemia was evaluated in rabbits using a semi-quantitative system for scoring ocular irritation modified from Hackett and McDonald (Hackett R, and McDonald, T. "Eye irritation," in *Advances in Modern Toxicology: Dermatoxicology*, F. Marzulli and H. Maibach, Eds., pp. 749-815, Hemisphere Publishing Corporation, Washington, D.C., USA, 4th edition, 1991). The ocular irritation was evaluated on a 4-point scale where 0=Normal: may appear blanched to reddish pink without perilimbal injection (except at 12 and 6 o'clock positions) with vessels of the palpebral and bulbar conjunctiva easily observed. +1=Mild: a flushed, reddish color predominantly confined to the palpebral conjunctiva with some perilimbal injection but primarily confined to the lower and upper parts of the eye from the 4 and 7 o'clock and the 11 and 1 o'clock positions. +2=Moderate: bright crimson red color of the palpebral conjunctiva with accompanying perilimbal injection covering at least 75% of the circumference of the perilimbal region. Individual vessels are not easily discernable. +3=Severe: dark, beefy red color with congestion of both the bulbar and the palpebral conjunctiva along with pronounced perilimbal injection. Petechiae may be present on the nictitating membrane and/or the upper palpebral conjunctiva.

Figure 8:
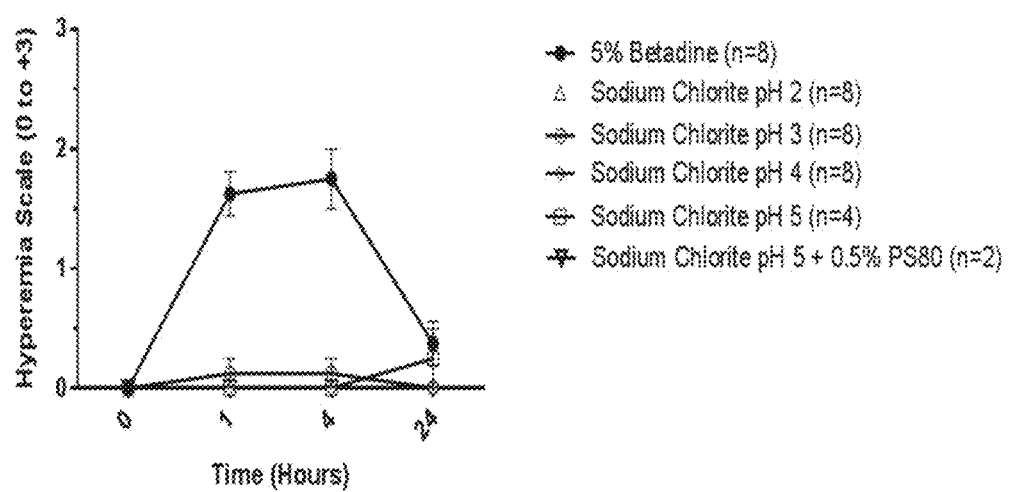
FIG. 8 shows ocular surface hyperemic response to sodium chlorite activated with buffers having different pH compared to 5% povidone-iodine ophthalmic solution or sodium chlorite in the presence of 0.5% polysorbate 80.

FIG. 8 shows ocular surface hyperemic response to sodium chlorite activated with buffers having different pH compared to 5% povidone-iodine or Sodium chlorite in the presence of 0.5% polysorbate 80 (PS80). 5% povidone-iodine and 5 formulations of 8000 ppm sodium chlorite activated using buffers of different pH (pH 2, pH 3, pH 4, pH 5, pH 5) and one in combination with 0.5% PS80 were evaluated for effects on ocular hyperemia over 24 hours. Eyes were unilaterally treated with a drop of proparacaine hydrochloride 0.5% for topical anesthesia prior to dosing with 250 ul of test formulation. Sodium chlorite was activated with buffers 5 minutes prior to dosing. Sodium chlorite was not washed out of the eye after dosing, unlike Betadine® which was washed out using several sterile saline flushes 2 minutes after dosing as per label. FIG. 8 shows that, unlike the sodium chlorite formulations, povidone-iodine was hyperemic: +1.5 score for 4 hours. Sodium chlorite having been activated with buffer having greater than or equal to pH 3, which elicited no response. Sodium chlorite activated with pH 2 buffer produced a trace response.

The OptoMotor™ system (Prusky G T, Alam N M, Beekman S, Douglas R M. Rapid quantification of adult and developing mouse spatial vision using a virtual optomotor system. *Invest Ophthalmol Vis Sci.* 2004; 45(12):4611-6.) was used to assess visual performance in conscious Dutch-Belted rabbits with normal vision. This system was designed as a tool for rapidly measuring the visual system of untrained and unrestrained mice and rats. The technique and apparatus was successfully adapted to rabbits. The system uses 4 large computer monitors to create a virtual reality chamber with three-dimensional projection arranged in a quadrangle around a testing arena. The rabbit is placed in a specially-designed restrainer in the chamber, near the center. A superimposed red crosshair is place between the eyes and the system centers the head for accuracy. For ease of direction, grating overlays are used. The test involves increasing the spatial frequency, in the cycles per degree (cpd), until the animal no longer tracks the grating indicating that the threshold or acuity is reached. System parameters are set to: Contrast=100%, starting spatial frequency=0.1 cpd and drift speed=12 d/s. Only visual acuity was recorded in this study of 12 rabbits that were divided into 2 groups of 6 each. Each group was treated unilaterally with a drop of Tetracaine Hydrochloride Ophthalmic Solution USP 0.5% (Bausch and Lomb, Tampa, Fla.) for topical anesthesia, then either with 50 ul of sodium chlorite 1600 ppm in citrate/borate buffer at pH ~7.6 or with 50 ul of Betadine® 5% Sterile Ophthalmic Prep Solution (povidone-iodine ophthalmic solution; Alcon, Fort Worth, Tex.). Povidone-iodine solution was washed out after 2 minutes of exposure with several sterile saline flushes. Contralateral eyes were untreated and served as controls. The study eye in each group was randomized as OD, n=3 or OS, n=3. OptoMotor™ visual acuities (spatial thresholds) were collected bilaterally at baseline and at 1, 2, 4 and 24 hours post treatment.

Figure 9:
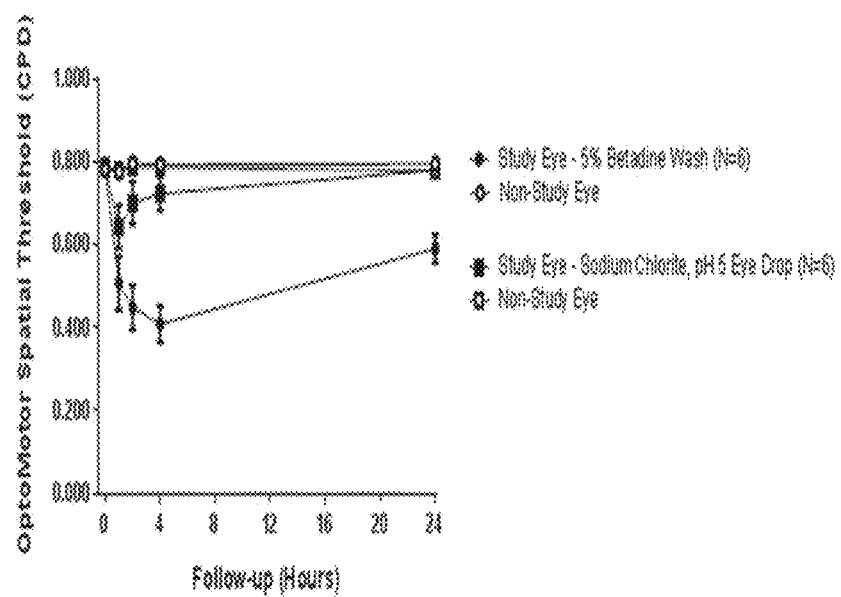
FIG. 9 shows effects of treatments for ocular disinfection on visual performance in rabbits.

FIG. 9 shows effects of treatments for ocular disinfection on visual performance in rabbits. The mean baseline thresholds were similar among study groups: Study eye=0.781±0.004 cpd and 0.784±0.007 cpd for povidone-iodine 5% and sodium chlorite 1600 ppm, respectively; non-study eye=0.782±0.006 cpd and 0.789±0.004 cpd, respectively. Povidone-iodine 5% decreased visual performance at each follow-up with a peak visual deficit of 0.38±0.04 cpd (0.30±0.06 log units) at 4 hours. Visual performance was still significantly reduced at 24 hours follow-up: −0.2±0.03 cpd (−0.13±0.02 log units). The peak visual deficit in the sodium chlorite 1600 ppm group occurred at 1 hour and was 0.14±0.06 cpd (0.09±0.05 log units), which was not statistically significant (p=0.06, paired Student's 't' test comparing study eye with non-study eye). Sodium chlorite 1600 ppm eye drop had less visual disturbance over a 24-hour period than a standard povidone-iodine 5% eye wash protocol in rabbits with normal vision.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements, embodiments, or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out the invention. Of course, variations on these described implementations will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

It is to be understood that the implementations disclosed herein are illustrative of the principles of the claims. Other modifications that may be employed are within the scope of the claims. Thus, by way of example, but not of limitation, alternative implementations may be utilized in accordance with the teachings herein. Accordingly, the claims are not limited to implementations precisely as shown and described.

P EMBODIMENTS

Embodiment P1

An antiseptic composition for disinfecting tissues, wherein the composition comprises sodium chlorite.

Embodiment P2

The antiseptic composition of clause 1, wherein the sodium chlorite is in an amount of about 800 ppm to about 8000 ppm.

Embodiment P3

The antiseptic composition of clause 1 or 2, wherein the sodium chlorite is activated in a buffer having a pH that is less than or equal to 5.

Embodiment P4

The antiseptic composition of clause 1 or 2, wherein the sodium chlorite is activated in a buffer having a pH that is up to about 7.6.

Embodiment P5

The antiseptic composition of any of clauses 1-4, further comprising a surfactant.

Embodiment P6

The antiseptic composition of clause 5, wherein the surfactant is a non-ionic surfactant in an amount of between 0.015% w/v to about 0.5% w/v.

Embodiment P7

The antiseptic composition of clause 6, wherein the non-ionic surfactant is selected from the group consisting of polyoxyethylene sorbitan monooleate, polyoxyethylene lauryl ether, and poly(ethylene glycol)-block-poly(propylene glycol)-block-poly(ethylene glycol).

Embodiment P8

The antiseptic composition of any of clauses 1-7, wherein the composition has antimicrobial activity.

Embodiment P9

The antiseptic composition of any of clauses 1-8, wherein the composition is in a form selected from the group consisting of aqueous solutions, emulsions (oil-in-water or water-in-oil), lotions, creams, ointments, salves, gels, instillations, foams, powders, tinctures, and solids.

Embodiment P10

The antiseptic composition of any of clauses 1-9, wherein the composition is in the form of an eye drop, eye wash, eye swab, or an eye bath.

Embodiment P11

The antiseptic composition of any of clauses 1-10, wherein the tissues disinfected comprise skin, eye, wound, or incision.

Embodiment P12

The antiseptic composition of any of clauses 1-10, wherein the tissues disinfected comprise an eye lid, eye brow, cheek, cornea, conjunctiva, or palpebral fornix.

Embodiment P13

The use of a composition for the preparation of a medicament for the disinfection of tissues, wherein the composition comprises sodium chlorite activated in a buffer.

Embodiment P14

The composition of clause 13, wherein the composition comprises the sodium chlorite in an amount of about 800 ppm to about 8000 ppm.

Embodiment P15

The composition of clause 13 or 14, wherein the buffer has a pH that is less than or equal to 5.

Embodiment P16

The composition of clause 13 or 14, wherein the buffer has a pH that is up to about 7.6.

Embodiment P17

The composition of any of clauses 13-16, wherein the composition comprises a surfactant.

Embodiment P18

The composition of clause 17, wherein the surfactant is a non-ionic surfactant in an amount of between 0.015% w/v to about 0.5% w/v.

Embodiment P19

The composition of clause 18, wherein the non-ionic surfactant is selected from the group consisting of polyoxyethylene sorbitan monooleate, polyoxyethylene lauryl ether, and poly(ethylene glycol)-block-poly(propylene glycol)-block-poly(ethylene glycol).

Embodiment P20

The composition of any of clauses 13-19, wherein the composition has antimicrobial activity.

Embodiment P21

The composition of any of clauses 13-20, wherein the composition is in a form selected from the group consisting of aqueous solutions, emulsions (oil-in-water or water-in-oil), lotions, creams, ointments, salves, gels, instillations, foams, powders, tinctures, and solids.

Embodiment P22

The composition of any of clauses 13-21, wherein the composition is in the form of an eye drop, eye wash, eye swab, or an eye bath.

Embodiment P23

The composition of any of clauses 13-22, wherein the tissues disinfected comprise skin, skin wound, or skin incision.

Embodiment P24

The composition of any of clauses 13-22 wherein the tissues disinfected comprise an eye lid, eye brow, cheek, cornea, conjunctiva, or palpebral fornix.

Embodiment P25

A method of treating tissues comprising topically applying an antiseptic composition comprising sodium chlorite activated in a buffer.

Embodiment P26

The method of clause 25, wherein the antiseptic composition comprises the sodium chlorite in an amount of about 800 ppm to about 8000 ppm.

Embodiment P27

The method of clause 25 or 26, wherein the sodium chlorite is activated in a buffer having a pH that is less than or equal to 5.

Embodiment P28

The method of clause 25 or 26, wherein the sodium chlorite is activated in a buffer having a pH that is up to about 7.6.

Embodiment P29

The method of any of clauses 25-28, wherein the antiseptic composition further comprises a surfactant.

Embodiment P30

The method of clause 29, wherein the surfactant is a non-ionic surfactant in an amount of between 0.015% w/v to about 0.5% w/v.

Embodiment P31

The method of clause 30, wherein the non-ionic surfactant is selected from the group consisting of polyoxyethylene sorbitan monooleate, polyoxyethylene lauryl ether, and poly(ethylene glycol)-block-poly(propylene glycol)-block-poly(ethylene glycol).

Embodiment P32

The method of any of clauses 25-31, wherein the antiseptic composition has antimicrobial activity.

Embodiment P33

The method of any of clauses 25-32, wherein the antiseptic composition is in a form selected from the group consisting of aqueous solutions, emulsions (oil-in-water or water-in-oil), lotions, creams, ointments, salves, gels, instillations, foams, powders, tinctures, and solids.

Embodiment P34

The method of any of clauses 25-33 wherein the antiseptic composition is in the form of an eye drop, eye wash, eye swab, or an eye bath.

Embodiment P35

The method of any of clauses 25-34, wherein the tissues disinfected comprise skin, skin wound, or skin incision.

Embodiment P36

The method of any of clauses 25-34, wherein the tissues disinfected comprise an eye lid, eye brow, cheek, cornea, conjunctiva, or palpebral fornix.

Embodiment P37

The use of the antiseptic composition of any of clauses 1-12 for the treatment of tissues.

Embodiment P38

The use of the antiseptic composition of any of clauses 1-12 for a treatment method as specified in any of clauses 25-36.

Embodiment P39

An ophthalmically acceptable topical composition for disinfecting ocular tissue, wherein the composition comprises: sodium chlorite in an amount of about 800 ppm to about 8000 ppm; a surfactant in an amount of about 0.015% w/v to about 0.5% w/v; and at least one buffer.

Embodiment P40

The composition of clause 39, wherein the surfactant is polyoxyethylene sorbitan monooleate.

Embodiment P41

The composition of clause 39, wherein the composition comprises about 8000 ppm sodium chlorite, about 0.5% w/v polyoxyethylene sorbitan monooleate, about 0.83% w/v sodium phosphate monobasic monohydrate, about 0.17% w/v citric acid monohydrate, hydrochloric acid and/or sodium hydroxide, and water; wherein the composition has a pH of about 5.

Embodiment P42

The composition of clause 39, wherein the composition comprises about 8000 ppm sodium chlorite, about 0.5% w/v polyoxyethylene sorbitan monooleate, about 0.25% w/v sodium phosphate monobasic monohydrate, about 0.35% w/v citric acid monohydrate, and water; wherein the composition has a pH of about 4.

Embodiment P43

The composition of clause 39, wherein the composition comprises about 8000 ppm sodium chlorite, about 0.5% w/v polyoxyethylene lauryl ether, about 0.83% w/v sodium phosphate monobasic monohydrate, about 0.17% w/v citric acid monohydrate, hydrochloric acid and/or sodium hydroxide, and water; wherein the composition has a pH of about 5.

Embodiment P44

The composition of clause 39, wherein the composition comprises about 8000 ppm sodium chlorite, about 0.5% w/v poly(ethylene glycol)-block-poly(propylene glycol)-block-poly(ethylene glycol), about 0.83% w/v sodium phosphate monobasic monohydrate, about 0.17% w/v citric acid monohydrate, hydrochloric acid and/or sodium hydroxide, and water; wherein the composition has a pH of about 5.

Embodiment P45

The composition of clause 39, wherein the at least one buffer is a phosphate buffer, a citrate buffer, or a borate buffer.

Embodiment P46

The composition of clause 39, wherein the composition has a pH less than or equal to 5.

Embodiment P47

A method for treating ocular tissue with an antiseptic composition comprising sodium chlorite and a surfactant.

Embodiment P48

The method of clause 47, wherein treating comprises topically applying the antiseptic composition to an eye of a patient.

Embodiment P49

The method of clause 48, wherein topically applying the antiseptic composition to the eye comprises topically applying the antiseptic composition prior to, during, and/or after a surgical procedure.

Embodiment P50

The ocular use of a composition comprising sodium chlorite and a surfactant.

Embodiment P51

The ocular use of the composition of clause 50, wherein the sodium chlorite is in an amount of about 800 ppm to about 8000 ppm.

Embodiment P52

The ocular use of the composition of clauses 50 or 51, wherein the surfactant is in an amount of about 0.015% w/v to about 0.5% w/v.

Embodiment P53

The ocular use of the composition of any one of clauses 50-52, wherein the composition further comprises at least one buffer having a pH of less than or equal to 5.

Embodiment P54

The ocular use of the composition of any one of clauses 50-53, wherein the composition is topically applied to an eye tissue.

Embodiment P55

The ocular use of the composition of clause 54, wherein the composition is topically applied to an eye tissue prior to, during, and/or after a surgical procedure of an eye.

Embodiment P56

A composition, method, or system substantially as shown and described herein.

What is claimed is:

1. An antiseptic composition consisting of a sodium chlorite stock solution, an activating buffer and, optionally, a surfactant, wherein:
   (a) the sodium chlorite stock solution consists of sodium chlorite, water and optionally one or more additional compounds selected from the group consisting of sodium chloride, sodium hydrogen carbonate, sodium formate, methanol, and sodium chlorate; and
   (b) the activating buffer consists of sodium phosphate monobasic monohydrate, sodium hydroxide, citric acid and water.

2. The antiseptic composition of claim 1, wherein the antiseptic composition has a sodium chlorite composition ranging from about 800 ppm to about 8000 ppm.

3. The antiseptic composition of claim 1, wherein the activating buffer has a pH that is less than or equal to 5.

4. The antiseptic composition of claim 1, wherein the activating buffer has a pH that is up to about 7.6.

5. The antiseptic composition of claim 1, wherein the surfactant is a non-ionic surfactant in an amount of between 0.015% w/v to about 0.5% w/v.

6. The antiseptic composition of claim 1, wherein the antiseptic composition is in the form of an eye drop, eye wash, eye swab, or an eye bath.

7. The antiseptic composition of claim 1, wherein the activating buffer has a pH ranging from 2 to 3.

8. The antiseptic composition of claim 1, wherein antiseptic composition has a pH ranging from 3 to 4.

9. The antiseptic composition of claim 1, wherein the sodium phosphate monobasic monohydrate is present in an amount of 0.15% w/v to 0.83% w/v.

10. The antiseptic composition of claim 1, wherein the citric acid is present in an amount of 0.17% w/v to 0.35% w/v.

11. The antiseptic composition of claim 1, wherein the antiseptic composition has a sodium chlorite concentration ranging from about 1600 ppm to about 8000 ppm.

12. The antiseptic composition of claim 1, wherein the antiseptic composition has a sodium chlorite concentration ranging from about 3200 ppm to about 6400 ppm.

* * * * *